United States Patent [19]

Badmin et al.

[11] 4,424,233
[45] Jan. 3, 1984

[54] PYRETHROID PESTICIDAL COMPOSITION

[75] Inventors: John S. Badmin, Isle of Sheppey; Barry J. Mears, Sittingbourne, both of England

[73] Assignee: Shell Oil Company, Houston, Tex.

[21] Appl. No.: 387,121

[22] Filed: Jun. 10, 1982

Related U.S. Application Data

[63] Continuation of Ser. No. 965,002, Nov. 30, 1978, abandoned.

[30] Foreign Application Priority Data

Apr. 12, 1978 [GB] United Kingdom ............... 14341/78

[51] Int. Cl.$^3$ ............................................ A01N 55/04
[52] U.S. Cl. .................................................. 424/288
[58] Field of Search ........................................ 424/288

[56] References Cited

U.S. PATENT DOCUMENTS

| 3,657,451 | 4/1972 | Horne, Jr. ........................... 424/288 |
| 3,973,035 | 8/1976 | Searle et al. ......................... 424/304 |
| 3,987,193 | 10/1976 | Davis et al. .......................... 424/305 |
| 3,996,244 | 12/1976 | Fujimoto et al. ............. 260/332.2 A |
| 4,024,163 | 5/1977 | Elliott et al. ..................... 260/347.4 |
| 4,100,297 | 7/1978 | Grandadum et al. ............... 424/304 |

FOREIGN PATENT DOCUMENTS 2753605  6/1978  Fed. Rep. of Germany ...... 424/304

Primary Examiner—Allen J. Robinson

[57] ABSTRACT

Compositions comprising (a) di[tri-(2-methyl-2-phenylpropyl)tin]oxide and (b) certain pyrethroid are useful pesticides, particularly against mites.

3 Claims, No Drawings

PYRETHROID PESTICIDAL COMPOSITION

This is a continuation of application Ser. No. 965,002, filed Nov. 30, 1978 now abandoned.

BACKGROUND OF THE INVENTION

1. Field of the Invention

The present invention relates to new pesticidal compositions comprising di[tri-(2-methyl-2-phenylpropyl)-tin]oxide and certain pyrethroids and to method of using such compositions to combat pests.

2. Description of the Prior Art

A number of organo-tin compounds are known to have miticidal activity. U.S. Pat. No. 3,657,451 describes a class of organo-tin miticides including di[tri-(2-methyl-2-phenylpropyl)-tin]oxide. On the other hand, there are literally hundreds of articles and patents directed to synthetic pyrethroids, and in particular to their use as insecticides. Examples of compounds of diverse chemical structures which demonstrate pyrethroid like activity are shown in U.S. Pat. Nos. 3,966,244 and 4,024,163. For certain uses an increase in the overall pesticidal spectrum of either the organo-tin or the pyrethroid compounds would be desirable.

SUMMARY OF THE INVENTION

The present invention provides an improved pesticidal composition which comprises:

(a) di[tri-(2-methyl-2-phenylpropyl)tin]oxide, hereinafter known as fenbutatin oxide, which has the formula:

(phenyl—C(CH$_3$)$_2$—CH$_2$—)$_3$SnOSn(—CH$_2$—C(CH$_3$)$_2$—phenyl)$_3$;

and (b) a pesticidally active pyrethroid having the following formula I $$A-\overset{O}{\underset{\|}{C}}-O-\overset{R}{\underset{|}{CH}}-\text{Ar}(X)_n \quad (I)$$

wherein A is an optionally-substituted aralkyl, alkyl or cycloalkyl group, R is hydrogen, cyano or ethynyl, X is alkyl, alkenyl, aralkyl or aryloxy, and n is 1 to 5.

An alkyl, cycloalkyl or alkenyl group represented by A or X preferably contains up to 6 carbon atoms, and an aralkyl or aryloxy group represented by A or X preferably contains up to 10 carbon atoms.

It should be noted that optical isomers, cis-trans isomers and other kinds of geometric isomers of the compounds according to formula I are within the scope of the present invention as well as racemates and mixtures of isomers of one or more of the pesticidally active compounds according to formula I. The various isomers of the compounds according to formula I may have different insecticidal toxicities and/or knock down potency. Thus, one may prefer to resolve mixtures of isomers to recover a more pesticidally active isomer or racemic mixture or to prepare the more active forms directly for use in the compositions of the invention.

When A represents an optionally-substituted cycloalkyl group, it preferably represents a cyclopropyl group of formula II $$\text{(II)}$$

(structure with $R_a$, $R_b$, $R_c$, $R_d$ and H substituents on cyclopropyl ring)

wherein $R_a$ and $R_b$ both represent an alkyl group having from 1 to 6 carbon atoms, especially a methyl group, or a halogen atom, especially a chlorine, bromine or fluorine atom; or $R_a$ and $R_b$ together represent an alkylene group having from 2 to 6, especially 3, carbon atoms; or $R_a$ represents a hydrogen atom and $R_b$ represents an alkenyl group having from 2 to 6 carbon atoms, especially an isobutenyl group, or a haloalkenyl group having from 2 to 6 carbon atoms and from 1 to 3 chlorine and/or bromine atoms, especially a monochlorovinyl, monobromovinyl, dichlorovinyl or dibromovinyl group; $R_c$ and $R_d$ both represent an alkyl group having 1 to 6 carbon atoms, especially a methyl group; or $R_c$ and $R_d$ together represent an alkylene group having from 2 to 6, especially 3, carbon atoms. Preferably $R_a$ and $R_b$ both represent a methyl group or a chlorine atom, or $R_a$ and $R_b$ together represent an alkylene group containing 3 carbon atoms, or $R_a$ represents a hydrogen atom and $R_b$ represents an isobutenyl group or an monochlorovinyl, monobromovinyl, dichlorovinyl or dibromovinyl group; and $R_c$ and $R_d$ both represent methyl groups or $R_c$ and $R_d$ together represent an alkylene group containing 3 carbon atoms.

When A in the formula I represents an optionally-substituted aralkyl group, it preferably represents a substituted benzyl group of formula III $$\text{(III)}$$

(benzyl structure with Z substituent on ring and —C(H)(Q)— group)

wherein Z represents a halogen, preferably chlorine, atom, or an alkoxy group of 1 to 4 carbon atoms, for example a methoxy group, and Q represents an alkyl group of 1 to 6 carbon atoms, especially a branched chain group, for example an isopropyl group. Preferably the group Z is in the 4-position of the benzene ring.

Preferably n represents 1 and X represents a phenoxy or benzyl group, especially a 3-phenoxy or 3-benzyl group.

The pesticidally active pyrethroids most preferred for use in the pesticidal composition according to the invention are pyrethroid insecticides having the formula I wherein A is alpha-isopropyl-4-chlorobenzyl, 2,2,3,3-tetramethylcyclopropyl, 2-(2,2-dichlorovinyl)-3,3-dimethylcyclopropyl, or 2-(2,2-dibromovinyl)-3,3-dimethylcyclopropyl; R is cyano; and n is 1 and X is 3-phenoxy. Especially preferred are the compounds designated Compounds X and Y in the example hereinafter.

The mixture of fenbutatin oxide and the pyrethroid insecticide not only produces a pesticide having a wider spectrum of activity than either component alone, but also produces a surprising synergistic effect especially with respect to acarids, e.g. glasshouse red spider mite, tetranychus urticae.

The weight ratio of the pyrethroid insecticide to fenbutatin oxide is preferably in the range of about 5:1 to about 1:50, more preferably in the range of about 1:1 to about 1:25 or even in the range of about 1:1 to about 1:5.

The pesticidal composition according to the invention preferably also comprises a carrier, especially at least two carriers, at least one of which is a surface-active agent.

A carrier may be a solid or liquid material, which may be inorganic or organic and of synthetic or natural origin. Typical solid carriers include natural and synthetic clays and silicates, for example natural silicas, for example, diatomaceous earths, and aluminum silicates, for example kaolinites, montmorillonites and micas. Typical liquid carriers are ketones, for example methylcyclohexanone, aromatic hydrocarbons, for example methylnaphthalenes, petroleum fractions, for example petroleum xylenes and light mineral oils, and chlorinated hydrocarbons, for example carbon tetrachloride. Mixtures of liquids are often suitable.

One or more surface-active agents and/or stickers can be included in the composition. A surface-active agent may be an emulsifying agent or a dispersing agent or a wetting agent; it may be non-ionic or ionic. Any of the surface-active agents usually applied in formulating insecticides may be used. Examples of suitable surface-active agents are the sodium and calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol, condensates of these with ethylene oxide and/or propylene oxide; condensation products of fatty alcohols or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates, such as sodium dodecylbenzene sulphonate; and polymers of ethylene oxide and copolymers of ethylene oxide and propylene oxide.

The composition of the invention may for example be formulated as a wettable powder, microcapsules, a dust, granules, a solution, an emulsifiable concentrate, an emulsion, a suspension concentrate or an aerosol. The composition may have controlled release properties, or may be suitable for use as a bait.

Wettable powders usually contain 25, 50 or 75% w of active ingredient and may contain, in addition to inert solid material, 3–10% w of a dispersing agent and, where necessary, 0–10% w of a stabiliser, a penetrant and/or a sticker. A dust is usually formulated as a dust concentrate having a composition similar to that of a wettable powder but without a dispersant, and is diluted in the field with further solid carrier to give a composition usually containing ½–10% w of active ingredient.

Granules usually have a size in the range of from 10 to 100 BS mesh (1.676–0.152 mm) and may be manufactured by agglomeration or impregnation techniques. Generally, granules will contain ½–25% w active ingredient and 0–10% w of additives, for example a stabiliser, slow release modifier and/or a binding agent.

Emulsifiable concentrates usually contain, in addition to a solvent, and, when necessary, co-solvent, 10–50% w/v active ingredient, 2–20% w/v emulsifier and 0–20% w/v of other additives, for example a stabiliser, a penetrant and/or a corrosion inhibitor. A suspension concentrate is a stable, non-sedimenting, flowable product and usually contains 10–75% w active ingredient, 0.5–15% w of dispersing agent, 0.1–10% w of suspending agent, for example protective colloid and for a thioxotropic agent, and 0–10% w of other additives including, for example, a defoamer, a corrosion inhibitor, a stabiliser, a penetrant and/or a sticker, and a dispersant, water or an organic liquid in which the active ingredient is substantially insoluble; certain organic additives and/or inorganic salts may be dissolved in the dispersant to assist in preventing sedimentation or as anti-freeze for water.

The aqueous dispersions and emulsions formed by diluting a wettable powder or an emulsifiable concentrate of the invention with water, also lie within the scope of the present invention. Such dispersions and emulsions may be of the water-in-oil or of the oil-in-water type, and may have a thick "mayonnaise"-like consistency.

A composition of the invention may also contain other ingredients, for example, one or more other compounds possessing pesticidal, herbicidal or fungicidal properties, or attractants, for example pheromones or food ingredients, for use in baits and trap formulations.

The invention also includes a method of combating pests at a locus which comprises applying to that locus a pesticidal composition according to the invention.

The invention is further illustrated by the following Example in which the joint action of two pesticides was analysed according to the method of Yun-Pei Sun and E. R. Johnson, Journal of Economic Entomology, 1960, Volume 53, No. 5, pages 887–892.

Thus, the joint action of two pesticides was analysed by determining the actual toxicity indices of the individual compounds and of mixtures of the compounds by reference to dosage-mortality curves. The theoretical toxicity of the mixture is equal to the sum over both components of the percentage of each individual compound multiplied by its respective toxicity index. Therefore:

$$\text{Co-toxicity coefficient of mixture} = \frac{\text{Actual toxicity index of mixture}}{\text{Theoretical toxicity index of mixture}} \times 100$$

A coefficient of a mixture near 100 indicates the probability of similar action by the two pesticides; independent action usually gives a coefficient less than 100, while a coefficient significantly above 100 strongly indicates synergism.

The pyrethroid insecticides in the Example are shown below.

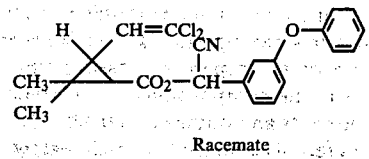

Compound X

Racemate

-continued

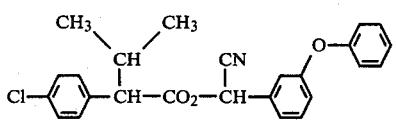

Compound Y

Racemate

EXAMPLE

Activity of Pyrethroid/Fenbutatin Oxide mixtures against *Tetranychus urticae* (Glasshouse Red Spider Mite)

The acaricidal activities of fenbutatin oxide, Compound X, Compound Y and mixtures thereof were assessed by the following method.

The compounds and mixtures were formulated as solutions or suspensions in water containing 20% by weight of acetone and 0.05% by weight of Triton X-100 TM as wetting agent. The resulting compositions contained 0.4% by weight of the compound or mixture to be tested, and were subsequently diluted to produce compositions containing various concentrations. Leaf discs cut from french bean plants were sprayed with the compositions and left for ½ to 1 hour drying period. Each leaf disc was then innoculated with 10 red spider mites and mortality counts made 24 hours after innoculation. From these results the $LC_{50}$'s (the lethal concentration in micrograms of active material per milliliter required to kill 50% of the mite population) could be calculated.

The toxicity indices of the compounds and the mixtures were calculated using the following formula and using fenbutatin oxide itself as the standard:

$$\text{Toxicity Index} = \frac{LC_{50} \text{ of standard}}{LC_{50} \text{ of compound or mixture}}$$

The coefficients of cotoxicity were then calculated according to the method described above. The results are shown in the following Table.

TABLE

Activity against *Tetranychus Urticae*

| Treatment | $LC_{50}$ | Toxicity Index | Coefficient of Cotoxicity (for mixtures) |
|---|---|---|---|
| Fenbutatin Oxide | 0.038 | 100 | |
| Compound X | 0.21 | 18 | |
| Compound Y | 0.24 | 16 | |
| Fenbutatin Oxide + Compound X (1:5 weight ratio) | 0.96 | 39 | 124 |
| Febutatin Oxide + Compound Y (1:5 weight ratio) | 0.84 | 45 | 151 |

It can be seen that the coefficients of cotoxicity are in both cases clearly in excess of 100, thus demonstrating the synergistic effect of the pyrethroid/fenbutatin oxide mixtures.

We claim:
1. An acaricidal composition comprising as the essential active ingredients
 (a) di[tri-(2-methyl-2-phenylpropyl)tin]oxide; and
 (b) alpha-cyano-3-phenoxybenzyl alpha-isopropyl-p-chlorophenyl-acetate in a ratio of (b) to (a) of from about 1 to 5.
2. A composition according to claim 1 which includes at least one carrier or surface-active agent.
3. A method of combating acarid pests which comprises applying to the pests or pest-infested plant or animal an acaricidally-effective amount of a composition as claimed in claim 1.

* * * * *